United States Patent [19]
Nichols et al.

[11] Patent Number: 5,959,110
[45] Date of Patent: *Sep. 28, 1999

[54] FUSED ISOQUINOLINES AS DOPAMINE RECEPTOR LIGANDS

[75] Inventors: David E. Nichols, West Lafayette, Ind.; Richard Mailman, Chapel Hill, N.C.; Debasis Ghosh, Indianapolis, Ind.

[73] Assignees: Purdue Research Foundation, West Lafayette, Ind.; University of North Carolina, Chapel Hill, N.C.

[ * ] Notice: This patent issued on a continued prosecution application filed under 37 CFR 1.53(d), and is subject to the twenty year patent term provisions of 35 U.S.C. 154(a)(2).

[21] Appl. No.: 08/727,451

[22] PCT Filed: Aug. 16, 1996

[86] PCT No.: PCT/US96/13416

§ 371 Date: Aug. 16, 1996

§ 102(e) Date: Aug. 12, 1996

[87] PCT Pub. No.: WO97/06799

PCT Pub. Date: Feb. 27, 1997

Related U.S. Application Data
[60] Provisional application No. 60/002,519, Aug. 18, 1995.

[51] Int. Cl.$^6$ .................. C07D 221/18; C07D 491/056
[52] U.S. Cl. ................................. 546/75; 546/48
[58] Field of Search ................ 546/66, 48, 75; 514/288, 280

[56] References Cited

U.S. PATENT DOCUMENTS

| | | | |
|---|---|---|---|
| 4,346,090 | 8/1982 | Humber et al. | 514/280 |
| 5,047,536 | 9/1991 | Nichols | 546/61 |
| 5,420,134 | 5/1995 | Nichols et al. | 514/280 |

FOREIGN PATENT DOCUMENTS
WO 92/04356  3/1992  WIPO.

OTHER PUBLICATIONS
Ghosh et al. Jour. Med. Chem. vol. 39 pp. 549–555, 1996.
Dorland's Illustrated Medical Dictionary 26$^{th}$ Ed Saunders, Philadelphia, pp. 401 and 856, 1981.

Sami, et al., "Amino–substituted 2–[2'–(dimethylamino)ethyl]–1,2–dihydro–3H–debenz[de,h]isoquinoline–1,3–diones. Synthesis, Antitumor Activity, and Quantitative Structure–Activity Relationship," Mar. 13, 1995, *J. Med. Chem.,* vol. 38, No. 6, pp. 983–993.

Brewster, et al., "trans–10,11–Dihydroxy–5,6,6a,7,8, 12b–hexahydrobenzo[a]phenanthridine: A Highly Potent Selective Dopamine $D_1$ Full Agonist," 1990, *J. Med. Chem.,* vol. 33, No. 6, pp. 1756–1764.

Riggs, et al., "Specific Dopamine D–1 and $DA_1$ Properties of 4–(Mono– and –dihydroxyphenyl)–1,2,3,4–tetrahydroisoquinoline and Its Tetrahydrothieno[2,3–c]pyridine Analogue," 1987, *J. Med. Chem.,* vol. 30, No. 8, pp. 1454–1458.

Sami, et al., "2–substituted 1,2–dihydro–3H–dibenz[de,h] isoquinoline–1,3–diones. A new Class of Antitumor Agent." Mar. 19, 1993, *J. Med. Chem.,* vol. 36, No. 6, pp. 765–770.

*Primary Examiner*—John M. Ford
*Attorney, Agent, or Firm*—Barnes & Thornburg

[57] ABSTRACT

The present invention is directed to a novel dopamine receptor ligands of the formula:

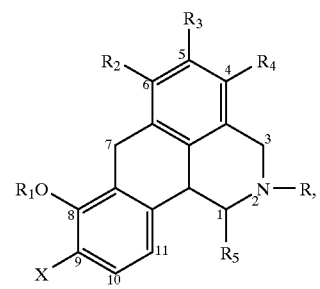

pharmaceutical formulations of such compounds, and a method using such compounds for treating a patient suffering from dopamine-related dysfunction of the central or peripheral nervous system.

10 Claims, 4 Drawing Sheets

Scheme 1

FUSED ISOQUINOLINES AS DOPAMINE RECEPTOR LIGANDS

CROSS REFERENCE TO RELATED APPLICATIONS

This application is a Section 371(e) counterpart of International Application No. PCT/US96/13416, filed Aug. 16, 1996, which claims priority to U.S. Provisional Application Ser. No. 60/002,519, filed Aug. 18, 1995.

This invention was made with Government support under Grant No. MH-42705 awarded by the National Institute of Health. The Government has certain rights in the invention.

FIELD OF THE INVENTION

This invention is directed to novel ligands for dopamine receptors. More particularly, the present invention is directed to optionally substituted tetrahydro-1H-naph[1,2,3-de]isoquinoline compounds and their use in pharmaceutical formulations for treatment of dopamine-related dysfunction of the central and peripheral nervous system.

BACKGROUND AND SUMMARY OF THE INVENTION

Dopamine, a neurotransmitter in the central nervous system, has been implicated in numerous neurological disorders. For example it has been hypothesized that excess stimulation of dopamine receptor subtypes may be linked to schizophrenia. Additionally, it is generally recognized that either excessive or insufficient functional dopaminergic activity in the central and/or peripheral nervous system may cause hypertension, narcolepsy, and other behavioral, neurological, physiological, and movement disorders including Parkinson's disease, a chronic, progressive disease characterized by an inability to control the voluntary motor system.

Dopamine receptors have traditionally been classified into one of two families ($D_1$ and $D_2$) based on pharmacological and functional evidence. $D_1$ receptors preferentially recognize the phenyltetrahydrobenzazepines and lead to stimulation of the enzyme adenylate cyclase, whereas $D_2$ receptors recognize the butyrophenones and benzamides and are coupled negatively (or not at all) to adenylate cyclase. It is now known that several subtypes of dopamine receptors exist and at least five genes code for subtypes of dopamine receptors: $D_1$, $D_2$, $D_3$, $D_4$ and $D_5$. The traditional classification, however, remains useful, with the $D_1$-like class comprising the $D_1$ ($D_{1A}$) and the $D_5$ ($D_{1B}$) receptors, whereas the $D_2$-like class consists of the $D_2$, $D_3$ and $D_4$ receptors.

Central nervous system drugs exhibiting affinity for the dopamine receptors are generally classified not only by their receptor selectivity, but further by their agonist (receptor stimulating) or antagonist (receptor blocking) activity. While the physiological activities associated with the interaction of dopamine with the various receptor subtypes are not fully understood, it is known that ligands exhibiting selectivity for a particular receptor subtype will produce more or less predicable neuropharmaceutical results. The availability of selective dopamine receptor antagonist and agonist compounds will enable the design of experiments to enhance understanding of the manifold functional roles of $D_1$ receptors and lead to new treatments for various central and peripheral nervous system disorders.

Initially, studies of dopamine receptors were focused on the $D_2$ family, however the critical role of the dopamine $D_1$ receptor in nervous system function has recently become apparent. Early work on selective $D_1$ receptor ligands primarily focused on molecules from a single chemical class, the phenyltetrahydrobenzazepines, such as the antagonist SCH23390 (1):

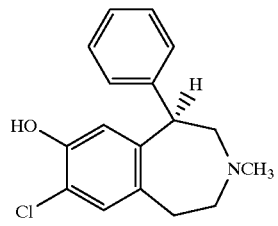

Several of the phenyltetrahydrobenzazepines were found to be $D_1$ receptor agonists; however, the agonists derived from this class [including for example SKF38393 (+)-2] generally lacked full intrinsic efficacy. Even SKF82958, purported to be a full agonist, recently has been shown not to have full intrinsic efficacy in preparations with decreased receptor reserve. The differentiation between agonists of full and partial efficacy is important to the medical research community due to the difference in the effect these compounds have on complex central nervous system mediated events. For example, dihydrexidine and the full agonist, A-77636, have exceptional anti-parkinsonian effects in the MPTP-treated monkey model, whereas partial agonists are without significant activity. More recent data suggest that full and partial agonists also differ in their effects on other complex neural functions.

Accordingly, researchers have directed their efforts to design ligands that are full agonists, having full intrinsic efficacy. One such compound is dihydrexidine (3), a hexahydrobenzo[a]phenanthridine of the formula:

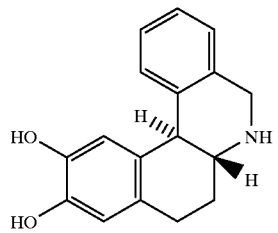

The structure of dihydrexidine (3) is unique from other $D_1$ agonists because the accessory ring system is tethered, making the molecule relatively rigid. Molecular modeling studies of dihydrexidine (3) have shown that the compound has a limited number of low energy conformations, in all of which the aromatic rings are held in a relatively coplanar arrangement. The recent elucidation of the configuration of the active enantiomer of dihydrexidine (3) was consistent with predictions from this model.

Unlike other high affinity, high intrinsic activity $D_1$ agonists like 3-substituted aminomethylisochromans, dihydrexidine (3) provided a semi-rigid template for developing a dopamine ligand model. The essential features of this model include the presence of a transoid β-phenyldopamine moiety, an equatorially oriented electron lone pair on the basic nitrogen atom, and near coplanarity of the pendant phenyl ring with the catechol ring. The dihydrexidine-based model has a transoid β-phenyldopamine moiety, whereas the dopaminergic phenyltetrahydrobenzazepines have a cisoid β-phenyldopamine conformation. The dihydrexidine-based model has served as the basis for the design of additional $D_1$ receptor agonists. The design and synthesis of $D_1$ receptor agonists having high intrinsic activity is important to the medical research community due to the potential use of full agonists to treat complex central nervous system mediated events and also conditions in which peripheral dopamine receptors are involved. For example, the compositions of the present invention have potential use as agents for lowering blood pressure.

One embodiment of the present invention is a novel class of dopamine receptor agonists of the general formula:

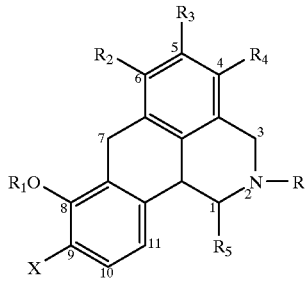

and pharmaceutically acceptable salts thereof, and pharmaceutical formulations of such compounds. The present compounds are useful for treating patients having a dopamine-related dysfunction of the central nervous system, and also conditions in which peripheral dopamine receptors are involved, as evidenced by an apparent neurological, psychological, physiological, or behavioral disorder.

DETAILED DESCRIPTION OF THE INVENTION

Figure 1:
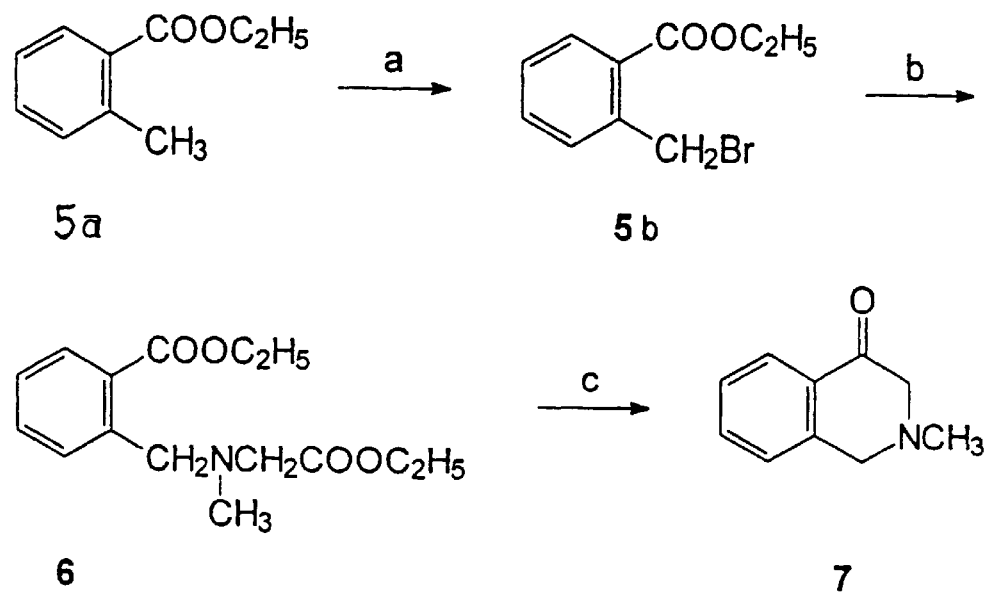
FIG. 1 illustrates the chemical reaction steps of scheme 1, converting ethyl-o-toluate to 2-methyl-2,3-dihydro-4(1H)-isoquinolone. Reagents: a) NBS, benzoylperoxide, $CCl_4$, reflux; b) sarcosine ethylester HCl, $K_2CO_3$, acetone; c) i. NaOEt, EtOH, reflux, ii. HCl, reflux.

There is provided in accordance with the present invention a compound of the general formula:

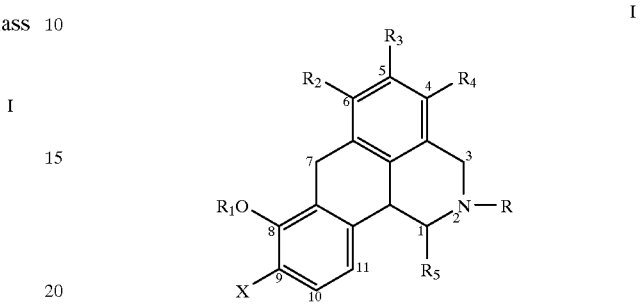

and pharmaceutically acceptable salts thereof wherein R and $R_5$ are hydrogen or $C_1$–$C_4$ alkyl; $R_1$ is hydrogen, $C_1$–$C_4$ alkyl or a phenoxy protecting group; X is hydrogen, halo or a group of the formula —$OR_6$ wherein $R_6$ is hydrogen, $C_1$–$C_4$ alkyl or a phenoxy protecting group, and $R_2$, $R_3$ and $R_4$ are independently selected from the group consisting of hydrogen, $C_1$–$C_4$ alkyl, phenyl, halo, or a group —$OR_1$ wherein $R_1$ is as defined above, and when X is a group of the formula —$O_6$, the groups $R_1$ and $R_6$ can be taken together to form a group of the formula —$CH_2$—.

The term "$C_1$–$C_4$ alkyl" as used herein refers to branched or straight chain alkyl groups comprising one to four carbon atoms, including, but not limited to, methyl, ethyl, propyl, isopropyl, n-butyl, t-butyl and cyclopropylmethyl.

The term "pharmaceutically acceptable salts" refers to those salts formed using organic or inorganic acids which salts are suitable for use in humans and lower animals without undesirable toxicity, irritation, allergic response and the like. Acids suitable for forming pharmaceutically acceptable salts of biologically active compounds having amine functionability are well known in the art. The salts can be prepared according to conventional methods in situ during the final isolation and purification of the present compounds, or separately by reacting the isolated compounds in free base form with a suitable salt forming acid.

The term "phenoxy protecting group" as used herein refers to substituents on the phenolic oxygen which prevent undesired reactions and degradations during synthesis and which can be removed later without effect on other functional groups on the molecule. Such protecting groups and the methods for their application and removal are well known in the art. They include ethers, such as cyclopropylmethyl, cyclohexyl, allyl ethers and the like; alkoxyalkyl ethers such as methoxymethyl or methoxyethoxymethyl ethers and the like; alkylthioalkyl ethers such a methylthiomethyl ethers; tetrahydropyranyl ethers; arylalkyl ethers such as benzyl, o-nitrobenzyl, p-methoxybenzyl, 9-anthrylmethyl, 4-picolyl ethers and the like; trialkylsilyl ethers such as trimethylsilyl, triethylsilyl, t-butyldimethylsilyl, t-butyldiphenylsilyl ethers and the like; alkyl and aryl esters such as acetates, propionates, n-butyrates, isobutyrates, trimethylacetates, benzoates and the like; carbonates such as methyl, ethyl, 2,2,2-trichloroethyl, 2-trimethylsilylethyl, benzyl and the like; and carbamates such as methyl, isobutyl, phenyl, benzyl, dimethyl and the like.

The term "$C_1$–$C_4$ alkoxyl" as used herein refers to branched or straight chain alkyl groups comprising one to four carbon atoms bonded through an oxygen atom, including but not limited to, methoxy, ethoxy, propoxy and t-butoxy.

Further, in accordance with other embodiments of this invention the present compounds can be formulated in conventional drug dosage forms for use in methods for treating a patient suffering from dopamine-related dysfunction of the central or peripheral nervous system. Effective doses of the present compounds depend on many factors, including the indication being treated, the route of administration, and the overall condition of the patient. For oral administration, for example, effective doses of the present compounds are expected to range from about 0.1 to about 50 mg/kg, more typically about 0.5 to about 25 mg/kg. Effective parenteral doses can range from about 0.01 to about 5 mg/kg of body weight. In general, treatment regimens utilizing compounds in accordance with the present invention comprise administration of from about 1 mg to about 500 mg of the compounds of this invention per day in multiple dose or in a single dose.

Liquid dose forms for oral administration may include pharmaceutically acceptable emulsions, microemmulsions, solutions, suspensions, and syrups containing inert diluents commonly used in the art, such as water. Such compositions may also comprise adjuvants such as wetting agents, emulsifying and suspending agents, sweetening, and flavoring agents. Injectable preparations of the compounds of the present invention can be formulated utilizing art-recognized products by dispersing or dissolving an effective doses of the compound in a parenterally acceptable diluent such as water, or more preferably isotonic sodium chloride solution. The parenteral formulations can be sterilized using art-recognized microfiltration techniques.

The compounds of this invention can also be formulated as solid dosage forms for oral administration such as capsules, tablets, powders, pills and the like. Typically the active compound is admixed with an inert diluent or carrier such as sugar or starch and other excipients appropriate for the dosage form. Thus tableting formulations will include acceptable lubricants, binders and/or disintegrants. Optionally powder compositions comprising an active compound of this invention and, for example, a starch or sugar carrier can be filled into gelatin capsules for oral administration. Other dosage forms of the compounds of the present invention can be formulated using art-recognized techniques in forms adapted for the specific mode of administration.

Figure 2:
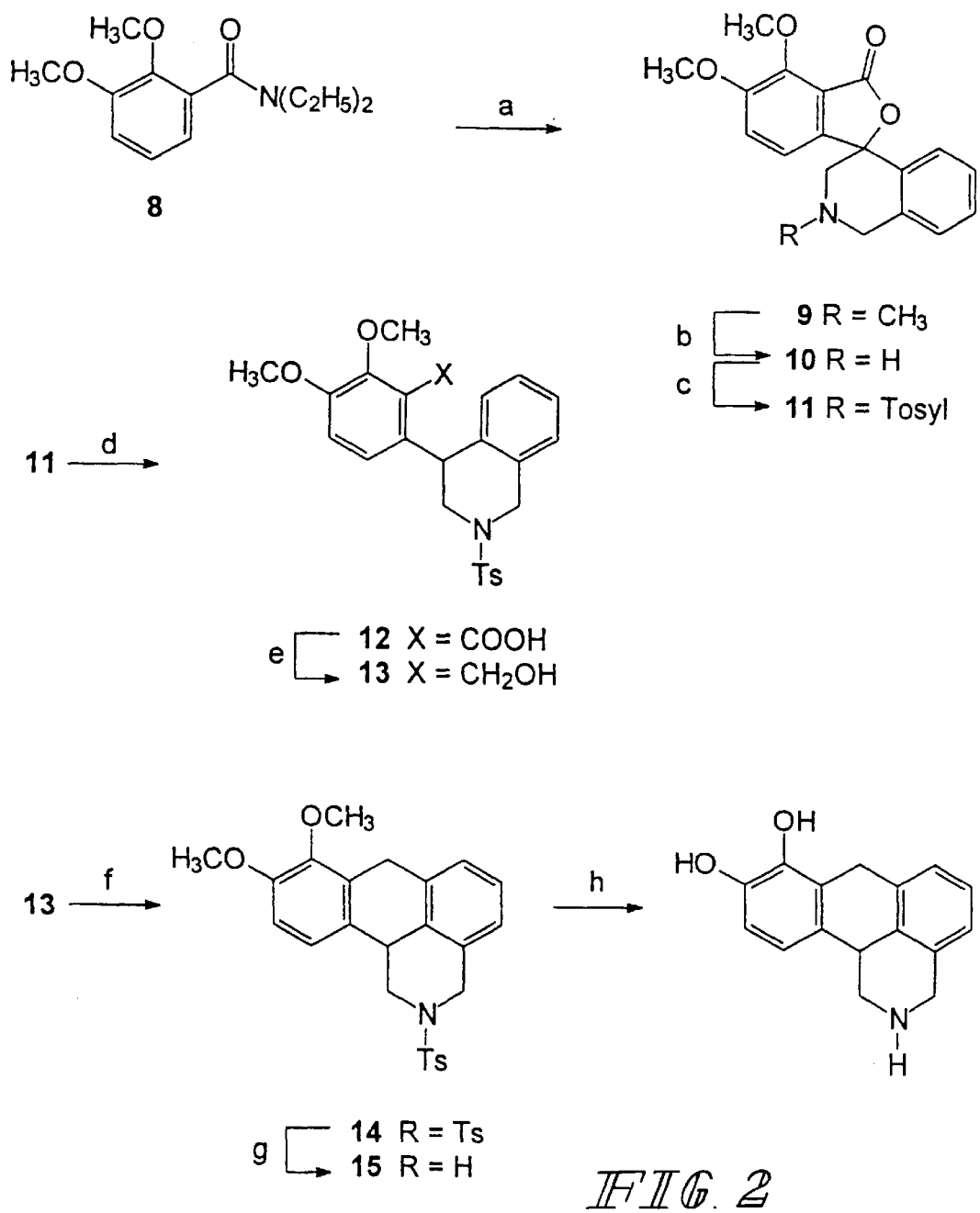
FIG. 2 illustrates the chemical reaction steps of scheme 2, converting 2,3-dimethoxy-N,N'-diethylbenzamide to dinapsoline. Reagents: a) i. sec-butyllithium, TMEDA, $Et_2O$, −78° C., ii. Compound 7, iii. TsOH, Toluene, reflux; b) i. 1-chloroethylchloroformate, $(CH_2Cl)_2$, ii. $CH_3OH$; c) TsCl, $Et_3N$; d) $H_2$/Pd—C, HOAc; e) $BH_3$—THF; f) concd $H_2SO_4$, −40° C. to −5° C.; g) Na—Hg, $CH_3OH$, $Na_2HPO_4$; h)$BBr_3$, $CH_2Cl_2$.

One compound provided in accordance with the present invention is (±)-8,9-dihydroxy-2,3,7,11b-tetrahydro-1H-naphtho[1,2,3-de]isoquinoline denominated hereinafter as "dinapsoline." Dinapsoline is synthesized from 2-methyl-2,3-dihydro-4(1H)-isoquinolone according to the procedure depicted generally in FIGS. 1 and 2. Side chain bromination of ethyl-o-toluate (5a) with NBS in the presence of benzoyl peroxide produced compound 5b. Alkylation of sarcosine ethyl ester with compound 5b afforded compound 6, which after Dieckmann condensation and subsequent decarboxylation on acidic hydrolysis yielded compound 7.

As shown in Scheme 2 (FIG. 2), ortho directed lithiation of 2,3-dimethoxy-N,N'-diethylbenzamide (8) with sec-butyllithium/TMEDA in ether at −78° C. and condensation of the lithiated species with compound 7 followed by reflux with p-toluene sulfonic acid gave spirolactone, 9 in modest yield. N-Demethylation of 9 with 1-chloroethylchloroformate followed by methanolysis of the intermediate afforded compound 10, which on treatment with p-toluene sulfonyl chloride and triethylamine provided compound 11.

Early attempts to synthesize compound 11 directly by condensation of 2-p-toluene sulfonyl-2,3-dihydro-4(1H)-isoquinolone with lithiated compound 8 in THF or ether, followed by lactonization with acid provided only minute amounts (<5%) of compound 11. Enolization of 2-p-toluenesulfonyl-2,3-dihydro-4(1H)-isoquinolone under the basic reaction conditions is one obvious explanation for the poor yield.

Hydrogenolysis of compound 11 in glacial acetic acid in the presence of 10% palladium on carbon gave compound 12, which on reduction with diborane afforded intermediate compound 13. Cyclization of compound 13 with concentrated sulfuric acid at low temperature provided compound 14. N-Detosylation of compound 14 with Na/Hg in methanol buffered with disodium hydrogen phosphate gave compound 15. Finally, compound 15 was treated with boron tribromide to effect methyl ether cleavage yielding dinapsoline (4) as its hydrobromide salt.

Space-filling representations of the low energy conformations for (+)-trans-10,11-dihydroxy-5,6,6a,7,8,12b-hexahydrobenzo[a]phenanthridine [(+)-dihydrexidine] and the 11bR enantiomer of dinapsoline that is homochiral to (+)-dihydrexidine at its 12bS chiral center have been compared. Two major structural features are readily evident. First, the steric bulk provided by the C(7)–C(8) ethano bridge in dihydrexidine (3) has been removed. Second, the angle of the pendent phenyl ring with respect to the plane of the catechol ring is changed slightly. This is most evident, in face-on views, where the aromatic hydrogen H(1) in dihydrexidine (3) projects above the catechol ring. In dinapsoline however, this position is used to tether the pendent phenyl ring through a methylene unit, to the catechol ring; this forces the pendent phenyl ring to twist in a clockwise direction, relative to dihydrexidine (3), when viewed from above. The amino groups are in similar positions, given the degree of conformational flexibility of the heterocyclic rings. In addition, both molecules can present an N—H vector in an equatorial orientation, a feature of the pharmacophore believed to be important for $D_1$ receptor agonists. Consistent with those observations the pharmacological properties of these two molecules are similar.

Experiments have been conducted to determine the binding of dinapsoline at $D_1$ receptors. Dinapsoline was found to have almost identical affinity ($K_1$=5.9 nM) as dihydrexidine (3) for rat striatal $D_1$ receptors. In addition, competition experiments utilizing unlabeled SCH23390 (1) as a competitor demonstrated that dinapsoline competes with high affinity, having a shallow competition curve ($n_H$=0.66) that suggests agonist properties (see FIG. 3). The agonist properties of dinapsoline at $D_1$ receptors were confirmed in vitro by measuring the ability of dinapsoline to increase cAMP production in rat striatum and C-6-m$D_1$ cells (see experimental data presented below). In both rat striatum and C-6-m$D_1$ cells, dinapsoline has full agonist activity with an $EC_{50}$ of about 30 nM in stimulating synthesis of cAMP via $D_1$ receptors.

Thus the pharmacological data confirm that dinapsoline has high affinity for dopamine $D_1$ receptors labeled with [$^3$H]SCH23390 that is almost identical to that of (+)-trans-10,11-dihydroxy-5,6,6a,7,8,12b-hexahydrobenzo-[a]phenanthridine (dihydrexidine). Moreover, (+)-8,9-dihydroxy-2,3,7,11b-tetrahydro-1H-naphtho[1,2,3-de]-isoquinoline (dinapsoline), in both rat striatal membranes and in cloned expressed primate $D_{1A}$ receptors, was a full agonist relative to dopamine, similar to dihydrexidine (3) but unlike the partial agonist (+)-SKF38393 (see FIGS. 4 and 5: (+)-SKF38393=(+)-2; (±)-trans-10,11-dihydroxy-5,6, 6a,7,8,12b-hexahydrobenzo[a]phenanthridine=(+)-3, and (+)-8,9-dihydroxy-2,3,7,11b-tetrahydro-1H-naphtho[1,2,3-de]isoquinoline=4).

Based on the underlying model of the $D_1$ pharmacophore, it is anticipated that both the affinity and intrinsic activity of racemic dinapsoline (and substituted analogs thereof) reside in only one of its enantiomers— the 11bR absolute configuration (and its homochiral analogs). Resolution of the racemate using art recognized separation techniques is expected to yield one dinapsoline isomer with approximately twice the $D_1$ affinity exhibited by the racemate, thus making its affinity for the $D_1$ receptor similar to (+)-trans-10,11-dihydroxy-5,6,6a,7,8,12b-hexahydrobenzo[a]phenanthridine.

Figure 3:
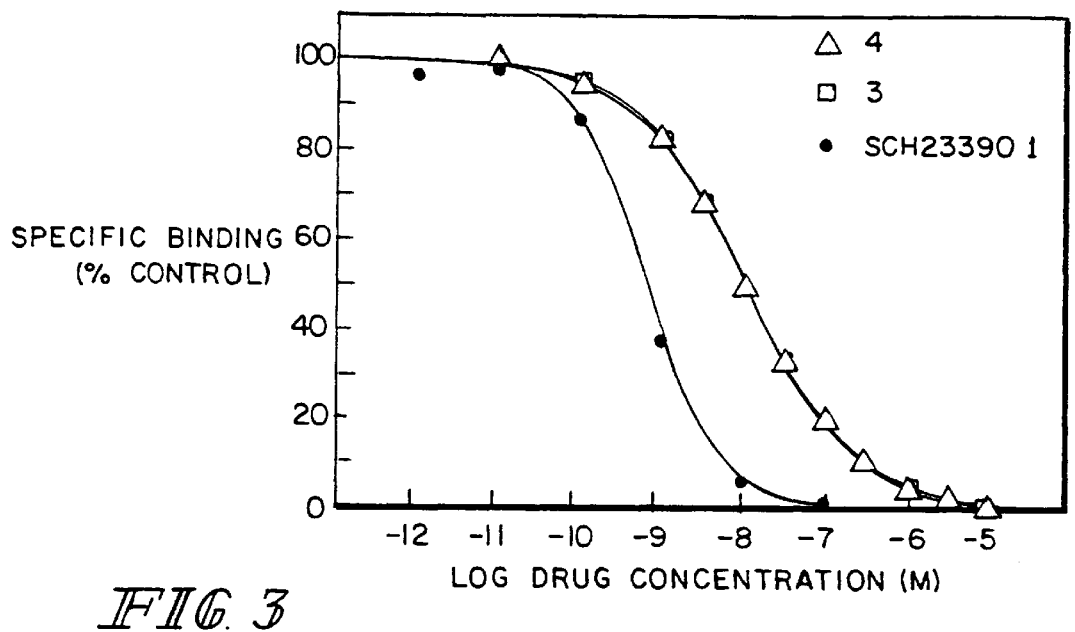
FIG. 3 is a graphic representation of the affinity of dinapsoline (triangles), (+)-dihydrexidine (squares) and (+)-SCH23390 (solid circles) for striatal $D_1$ receptors. Rat striatal $D_1$ receptors were labeled with [$^3$H]SCH23390 (1), and unlabeled dinapsoline, (+)-dihydrexidine or (+)-SCH23390 was added to determine the specific binding of each compound for the $D_1$ receptor.

As shown in FIG. 3 and Table 1, dinapsoline has greater affinity for $D_2$-like receptors than does dihydrexidine. When dihydrexidine was first synthesized, it was anticipated that it would be fairly selective for the $D_1$ vs. $D_2$-like receptors. However, dihydrexidine was determined to be only about ten-fold $D_1$:$D_2$ selective. In addition, dihydrexidine, while having the expected dopamine agonist activity, also had an unusual property termed herein as "functional selectivity". Specifically, in rats (in vivo or in vitro), dihydrexidine acts as an agonist at $D_2$-like receptors located post-synaptically, but as an antagonist at $D_2$-like receptors located pre-synaptically. Such is believed to be due to differences in the ligand-receptor-G protein complex located post-synaptically vs. pre-synaptically, as determined by the specific G proteins present in the given cellular milieu.

It has been shown that these $D_2$ properties of dihydrexidine reside in the same enantiomer (i.e., 6aR,12bS) that is the high affinity full agonist at the $D_1$ receptor. On this basis, it is expected that both the $D_1$ and $D_2$ properties of dinapsoline also reside in the homochiral enantiomer. The optical isomers of dinapsoline, and appropriate analogs, constitute significant tools to study the phenomena of "functional selectivity".

The antiparkinsonian effects of dihydrexidine in the MPTP model of Parkinson's disease have been previously reported, and it is anticipated that dinapsoline will show similar effects. Accordingly dinapsoline and its derivatives have potential clinical utility in Parkinson's Disease and in other conditions where perturbation of dopamine receptors may be therapeutic. In addition, it has been reported that appropriate modification of dihydrexidine will produce analogs that can be targeted to specific subpopulations of the dopamine receptor family. Similar strategies with dinapsoline should result in compounds with novel receptor subtype selectivity and/or functional profiles.

With reference to the following described experimental procedures, melting points were determined with a Thomas-Hoover melting point apparatus and are uncorrected. $^1$H NMR spectra were recorded with a Varian VXR 500S (500 MHz) NMR instrument and chemical shifts were reported in δ values (ppm) relative to TMS. The IR spectra were recorded as KBr pellets or as a liquid film with a Perkin Elmer 1600 series FTIR spectrometer. Chemical ionization mass spectra (CIMS) were recorded on a Finnigan 4000 quadruple mass spectrometer. High resolution CI spectra were recorded on Kratos MS50 spectrometer. Elemental analysis data were obtained from the microanalytical laboratory of Purdue University, West Lafayette, Ind.

THF was distilled from benzophenone-sodium under nitrogen immediately before use; 1,2-Dichloroethane was distilled from phosphorous pentoxide before use.

EXAMPLE 1

Preparation of 2-methyl-2,3-dihydro-4(1H)-isoquinolone

Ethyl 2-bromomethylbenzoate (5b)

A solution of ethyl-o-toluate (41.2 g, 0.25 mole) in carbon tetrachloride (200 mL) was added dropwise to a stirring mixture of benzoyl peroxide (100 mg), carbon tetrachloride (200 mL) and NBS (44.5 g, 0.25 mole) at 0° C. The mixture was heated at reflux for 3.5 h under nitrogen, and allowed to cool to room temperature overnight. The precipitated succinimide was removed by filtration and the filter cake was washed with carbon tetrachloride. The combined filtrates were washed successively with 2 N NaOH (100 mL), and water (2×100 mL), and the solution was dried over anhydrous $MgSO_4$, filtered (Celite), and evaporated under vacuum to yield the product as an oil. Drying under high vacuum overnight afforded 60.5 g (99%) of crude compound 5b; $^1$H NMR of the product showed the presence of ca. 15% of unreacted starting material. Since the mixture was not easily separable by chromatography or vacuum distillation it was used in the next step without further purification; $^1$H NMR (CDCl$_3$) δ1.43 (t, J=7 Hz, 3H, CH$_2$CH$_3$), 4.41 (q, J=7 Hz, 2H, CH$_2$CH$_3$), 4.96 (s, 1H, CH$_2$Br), 7.24 (m, 1H, ArH), 7.38 (m, 1H, ArH), 7.48 (m, 2H, ArH).

N-(2-carboethoxy)sarcosine ethyl ester (6)

To a mixture of sarcosine ethyl ester hydrochloride (32.2 g, 0.21 mole), potassium carbonate (325 mesh; 86.9 g, 0.63 mole), and acetone (800 mL) was added a solution of compound 5b (60.7 g; obtained from 0.25 mole of ethyl-o-toluate; 85% conversion to compound 6; calculated 0.21 mol) in acetone (100 mL) at room temperature under nitrogen. The mixture was stirred at reflux for 2 h and then left at room temperature for 20 h. The solid was removed by filtration (Celite) and the residue was washed with acetone. The filtrates were combined and evaporated under reduced pressure to afford an oil. The oil was dissolved in 250 mL of 3 N HCl and washed with ether. The aqueous layer was basified with aqueous. NaHCO$_3$, and extracted with ether (3×250 mL). Evaporation of the ether solution yielded an oil that was vacuum distilled to afford 45.33 g (77%) of compound 6: bp 140–142° C. (0.5 mm Hg) [bp 182–183° C. (10 mm Hg)]; $^1$H NMR (CDCl$_3$) δ1.24 (t, 3H, J=7.1 Hz, CH$_3$), 1.36 (t, 3H, J=7.1 Hz, CH$_3$), 2.35 (s, 3H, NCH$_3$), 3.27 (s, 2H, CH$_2$Ar), 4.00 (s, 2H, NCH$_2$), 4.14 (q, 2H, J=7.1 Hz, CH$_2$CH$_3$), 4.32 (q, 2H, J=7.1 Hz, CH$_2$CH$_3$), 7.28 (t, 1H, J=7.4 Hz, ArH), 7.42 (t, 1H, J=7.6 Hz, ArH), 7.52 (d, 1H, J=7.8 Hz, ArH), 7.74 (d, 1H, J=7.7 Hz, ArH).

2-Methyl-2,3-dihydro-4(1H)isoquinolone (7)

Freshly cut sodium (10.9 g, 0.47 g-atom) was added to absolute ethanol (110 mL) under nitrogen and the reaction was heated at reflux. After the metallic sodium had disappeared, a solution of compound 6 (35.9 g, 0.128 mole) in dry toluene (160 mL) was added slowly to the reaction mixture. It was then heated at reflux and ethanol was separated azeotropically via a Dean Stark trap. After cooling, the solvent was evaporated under reduced pressure. The remaining yellow semi-solid residue was dissolved in a mixture of water (50 mL), 95% ethanol (60 mL), and concentrated HCl (240 mL), and heated at reflux for 26 h. After cooling, the mixture was concentrated under vacuum and carefully basified with solid NaHCO$_3$. The basic solution was extracted with ether, dried (MgSO$_4$), and evaporated to an oil that was distilled to afford compound 7 (17.11 g, 83%): bp 130–132° C. (5 mm Hg) [bp 81–83° C. (0.4 mm Hg); mp (HCl) 250° C.]; IR (neat) 1694 (C=O) cm$^{-1}$; $^1$H NMR (CDCl$_3$) δ2.48 (s, 3H, CH$_3$), 3.31 (s, 2H, CH$_2$), 3.74 (s, 2H, CH$_2$), 7.22 (d, 1H, J=7.7 Hz, ArH), 7.34 (t, 1H, J=7.9 Hz, ArH), 7.50 (t, 1H, J=7.5 Hz, ArH), 8.02 (d, 1H, J=7.9 Hz, ArH).

Synthesis of 8,9-dihydroxy-2,3,7,11b-tetrahydro-1H-naphtho-[1,2,3-de]isoquinoline To a solution of 2,3-dimethoxy-N,N'-diethylbenzamide (compound 8) (14.94 g, 63 mmol) in ether (1400 mL) at −78° C. under nitrogen was added sequentially, dropwise, N,N,N',N'-tetramethylenediamine (TMEDA, 9.45 mL, 63 mmol), and sec-butyllithium (53.3 mL, 69 mmol, 1.3 M solution in hexane) through a rubber septum via syringe. After 1 h, freshly distilled compound 7 (10.1 g, 62.7 mmol) was added to the heterogenous mixture. The cooling bath was removed and the reaction mixture was allowed to warm to room temperature over 9 h. Saturated NH$_4$Cl solution (400 mL) was then added and the mixture was stirred for 15 min. The ether layer was separated and the water layer was extracted with dichloromethane (4×100 mL). The organic layers were combined, dried (MgSO$_4$), and evaporated to a brown oil. The oil was dissolved in toluene (500 mL), and heated at reflux for 8 h with 3.0 g of p-toluene sulfonic acid, cooled, and concentrated under vacuum. The residue was dissolved in dichloromethane, washed with dilute aqueous NaHCO$_3$, water, and then dried (Na$_2$SO$_4$), filtered and evaporated to a gummy residue. On trituration with ethyl acetate-hexane (50:50), a solid precipitated. Recrystallization from ethyl acetate-hexane afforded 12.75 g (63%) of compound 9 (2',3'-Dihydro-4,5-dimethoxy-2'-methylspiro[isobenzofuran-1(3H)-4'(1'H)isoquinoline]-3-one): mp 193–194° C.; IR (KBr) 1752 cm$^{-1}$ (C=O); $^1$H NMR (CDCl$_3$) δ2.47 (s, 3H, NCH$_3$), 2.88 (d, 1H, J=11.6 Hz), 3.02 (d, 1H, J=11.7 Hz), 3.76 (d, 1H, J=15.0 Hz), 3.79 (d, 1H, J=15.1 Hz), 3.90 (s, 3H, OCH$_3$), 4.17 (s, 3H, OCH$_3$), 6.83 (d, 1H, J=8.4 Hz, ArH), 7.03 (d, 1H, J=8.2 Hz, ArH), 7.11 (m, 3H, ArH), 7.22 (m, 1H, ArH); MS (CI) m/z 326 (100); Anal. (C$_{19}$H$_{19}$NO$_4$) C, H, N.

2',3'-Dihydro-4,5-dimethoxy-spiro[isobenzofuran-1(3H),4'(1'H) isoquinoline]-3-one (10)

1-chloro-ethylchloroformate (5.1 mL, 46.3 mmol) was added dropwise to a suspension of compound 9 (6.21 g, 19.2 mmol) in 100 mL of 1,2-dichloroethane at 0° C. under nitrogen. The mixture was stirred for 15 min at 0° C., and then heated at reflux for 8 h. The mixture was cooled, and concentrated under reduced pressure. To this mixture was added 75 mL of methanol and the reaction was heated at reflux overnight. After cooling, the solvent was evaporated under reduced pressure to afford the hydrochloride salt of compound 10 in nearly quantitative yield. It was sufficiently pure to use in the next step without further purification: mp (HCl) 220–222° C.; mp (base) 208–210° C.; IR (CH$_2$Cl$_2$, base) 1754 cm$^{-1}$ (C=O); $^1$H NMR (CDCl$_3$, base) δ3.18 (d, 1H, J=13.5 Hz), 3.30 (d, 1H, J=13.5 Hz), 3.84 (s, 3H, OCH$_3$), 3.96 (s, 3H, OCH$_3$), 4.02 (s, 2H, CH$_2$N), 6.67 (d, 1H, J=7.5 Hz, ArH), 7.12 (m, 2H, ArH), 7.19 (d, 1H, J=7.5 Hz, ArH), 7.26 (t, 1H, J=7.5 Hz, ArH), 7.41 (d, 1H, J=8.5 Hz, ArH); MS (CI) m/z 312 (100); HRCIMS Calculated for C$_{18}$H$_{17}$NO$_4$: 312.1236; Found 312.1198; Anal. (C$_{18}$H$_{17}$NO$_4$) H, N; C: calculated, 69.44; found, 68.01.

2',3'-Dihydro-4,5-dimethoxy-2'-p-toluenesulfonylspiro[isobenzofuran-1(3H),4'(1'H) isoquinoline]-3-one (11)

7 mL of triethylamine, was added dropwise to a mixture of p-toluenesulfonyl chloride (3.6 g, 18.9 mmole), compound 10 (as the HCl salt, obtained from 19.2 mmol of compound 9) and chloroform (100 mL) at 0° C. under nitrogen. After the addition was complete, the ice bath was removed and the reaction mixture was stirred at room temperature for 1 h. It was then acidified with 100 mL of cold aqueous 0.1 N HCl, extracted with dichloromethane (2×100 mL), and the organic extract was dried (MgSO$_4$), filtered, and evaporated under vacuum to afford a viscous liquid that on trituration with ethyl acetate-hexane at 0° C. gave a solid. Recrystallization from ethyl acetate-hexane afforded 8.74 g (97%, overall from compound 9) of compound 11: mp 208–210° C.; IR (KBr) 1767 cm$^{-1}$ (C=O); $^1$H NMR (CDCl$_3$) δ2.43 (s, 1H, CH$_3$), 3.22 (d, 1H, J=11 Hz), 3.88 (d, 1H, J=11 Hz), 3.90 (s, 3H, OCH$_3$), 3.96 (d, 1H, J=15 Hz), 4.17 (s, 3H, OCH$_3$), 4.81 (d, 1H, J=15 Hz), 6.97 (d, 1H, J=7.7 Hz, ArH), 7.16 (m, 3H, ArH), 7.26 (m, 1H, ArH), 7.38 (d, 2H, J=8 Hz, ArH), 7.72 (d, 2H, J=8 Hz, ArH); MS (CI) m/z 466 (100); Anal. (C$_{25}$H$_{23}$NO$_6$S) C, H, N.

3,4-Dimethoxy-6-[(2-p-toluenesulfonyl-1,2,3,4-tetrahydroisoquinoline)-4-yl]benzoic acid (12)

A solution of compound 11 (2.56 g, 5.51 mmol) in glacial acetic acid (250 mL) with 10% palladium on activated carbon (6.30 g) was shaken on a Parr hydrogenator at 50 psig for 48 h at room temperature. The catalyst was removed by filtration, and the solvent was evaporated to afford 2.55 g (99%) of compound 12 that was sufficiently pure to carry into the next step. An analytical sample was recrystallized from ethanol-water: mp 182–184° C.; IR (KBr) 1717 cm$^{-1}$ (COOH); $^1$H NMR (DMSO-d$_6$) δ2.35 (s, 3H, CH$_3$), 3.12 (m, 1H), 3.51 (dd, 1H, J=5, 11.5 Hz), 3.71 (s, 6H, OCH$_3$), 4.10 (m, 1H, Ar$_2$CH), 4.23 (s, 2H, ArCH$_2$N), 6.52 (d, 1H, J=7.5 Hz, ArH), 6.78 (d, 1H, J=7.5 Hz, ArH), 6.90 (m, 1H, ArH), 7.07 (t, 1H, J=8 Hz, ArH), 7.14 (t, 1H, J=6.5 Hz, ArH), 7.20 (d, 1H, J=7.5 Hz, ArH), 7.38 (d, 2H, J=8 Hz, ArH), 7.63 (d, 2H, J=8.5 Hz, ArH); MS (CI) m/z 468 (16), 450 (63), 296 (100); HRCIMS Calculated for C$_{25}$H$_{25}$NO$_6$S: 468.1481; Found 468.1467; Anal. (C$_{25}$H$_{25}$NO$_6$S) C, H, N.

2-N-p-Toluenesulfonyl-4-(2-hydroxymethyl-3,4-dimethoxyphenyl)-1,2,3,4-tetrahydroisoquinoline (13)

To a solution of compound 12 (1.4 g, 2.99 mmol) in dry tetrahydrofuran (30 mL) was added 1.0 M borane-tetrahydrofuran (8 mL) at 0° C. under nitrogen. After the addition was complete the mixture was stirred at reflux overnight. Additional diborane (4 mL) was added and stirring was continued for another 30 min. After cooling and evaporating under reduced pressure, methanol (30 mL) was carefully added, and the solvent was removed at low pressure. The process was repeated three times to ensure the methanolysis of the intermediate borane complex. Evaporation of the solvent gave 1.10 g (81%) of crude compound 13. An analytical sample was purified by flash chromatography (silica gel, EtOAc/Hexane) followed by recrystallization from ethyl acetate/hexane: mp 162–164° C.; $^1$H NMR (CDCl$_3$) δ2.38 (s, 3H, CH$_3$), 3.18 (dd, 1H, J=7.5, 11.9 Hz), 3.67 (dd, 1H, J=4.5, 11.8 Hz), 3.81 (s, 3H, OCH$_3$), 3.85 (s, 3H, OCH$_3$), 4.27 (d, 1H, J=15 Hz), 4.40 (d, 1H, J=15 Hz), 4.57 (t, 1H, J=6 Hz, CHAr$_2$), 4.71 (s, 2H, CH$_2$OH), 6.58 (d, 1H, J=8.5 Hz, ArH), 6.74 (d, 1H, J=8.6 Hz, ArH), 6.84 (d, 1H, J=7.7 Hz, ArH), 7.08 (t, 2H, J=7.6 Hz, ArH), 7.14 (t, 1H, J=6.6 Hz, ArH), 7.27 (d, 2H, J=8 Hz, ArH), 7.65 (d, 2H, J=8 Hz, ArH); MS (CI) m/z 454 (2.57), 436 (100); Anal. (C$_{25}$H$_{27}$NO$_5$S) C, H, N.

8,9-Dimethoxy-2-p-toluenesulfonyl-2,3,7,11b-tetrahydro-1H-napth[1,2,3-de]isoquinoline (14)

Powdered compound 13 (427 mg, 0.98 mmol) was added in several portions to 50 mL of cold concentrated sulfuric acid (50 mL) at −40° C. under nitrogen with vigorous mechanical stirring. After the addition, the reaction mixture was warmed to −5° C. over 2 h and then poured onto crushed ice (450 g) and left stirring for 1 h. The product was extracted with dichloromethane (2×150 mL), washed with water (2×150 mL), dried (MgSO$_4$), filtered and evaporated to afford an oil that on trituration with ether at 0° C. yielded compound 14 (353 mg, 82%) as a white solid that was used for the next step without further purification. An analytical sample was prepared by centrifugal rotary chromatography using 50% ethyl acetate-hexane as the eluent followed by recrystallization from EtOAc/Hexane: mp 204–206° C.; $^1$H NMR (CDCl$_3$) δ2.40 (s, 3H, CH$_3$), 2.80 (m, 1H, H-1a), 3.50 (dd, 1H, J=4.5, 17.5 Hz, H-1b), 3.70 (dd, 1H, J=7, 14 Hz, H-3a), 3.828 (s, 3H, OCH$_3$), 3.832 (s, 3H, OCH$_3$), 3.9 (m, 1H, H-11b), 4.31 (d, 1H, J=17.6 Hz, H-7a), 4.74 (ddd, 1H, J=1.7, 6.0, 11.2 Hz, H-7b), 4.76 (d, 1H, J=14.8 Hz, H-3b), 6.77 (d, 1H, J=8.3 Hz, ArH), 6.87 (d, 1H, J=8.4 Hz, ArH), 6.94 (d, 1H, J=7.6 Hz, ArH), 7.13 (t, 1H, J=7.5 Hz, Ar-H-5), 7.18 (d, 1H, J=7.2 Hz, ArH), 7.33 (d, 2H, J=8.1 Hz, ArH), 7.78 (d, 2H, J=8.2 Hz, ArH); MS (CI) m/z 436 (55), 198 (86), 157 (100); HRCIMS Calculated for $C_{25}H_{25}NO_4S$: 436.1583; Found 436.1570; Anal. ($C_{25}H_{25}NO_4S$) C, H, N.

8,9-Dimethoxy-2,3,7,11b-tetrahydro-1H-napth[1,2,3-de]isoquinoline (15)

A mixture of compound 14 (440 mg, 1.01 mmol), dry methanol (10 mL) and disodium hydrogen phosphate (574 mg, 4.04 mmol) was stirred under nitrogen at room temperature. To this mixture was added 6.20 g of 6% Na—Hg in three portions and the reaction was heated at reflux for 2 h. After cooling, water (200 mL) was added and the mixture was extracted with ether (3×200 mL). The ether layers were combined, dried (MgSO$_4$), filtered (Celite), and evaporated to give an oil that solidified under vacuum. After rotary chromatography 142 mg (50%) of compound 15 was obtained as an oil. The oil quickly darkened on exposure to air and was used immediately for the next step. A small portion of the oil was treated with ethereal HCl and the hydrochloride salt of compound 15 was recrystallized from ethanol-ether: mp (HCl salt) 190° C. (dec); $^1$H NMR (CDCl$_3$, base) δ3.13 (dd, 1H, J=10.8, 12 Hz, H-1a), 3.50 (dd, 1H, J=3.4, 17.4 Hz, H-1b), 3.70 (m, 1H, H-11b), 3.839 (s, 3H, OCH$_3$), 3.842 (s, 3H, OCH$_3$), 4.03 (dd, 1H, J=6, 12 Hz, H-7a), 4.08 (s, 2H, H-3), 4.33 (d, 1H, J=17.4 Hz, H-7b), 6.78 (d, 1H, J=8.24 Hz, ArH), 6.92 (m, 3H, ArH), 7.11 (t, 1H, J=7.5 Hz, ArH), 7.18 (d, 1H, J=7.5 Hz, ArH); MS (CI) m/z 282 (100); HRCIMS Calculated for $C_{18}H_{19}NO_2$: 282.1494; Found 282.1497.

8,9-Dihydroxy-2,3,7,11b-tetrahydro-1H-napth[1,2,3-de]isoquinoline (4)

To a solution of compound 15 (25 mg, 0.089 mmole) in dichloromethane (5 mL) at -78° C. was added boron tribromide (0.04 mL, 0.106 g, 0.42 mmol). After stirring at -78° C. under nitrogen for 2 h, the cooling bath was removed and the reaction mixture was left stirring at room temperature for 5 h. It was then cooled to -78° C. and methanol (2 mL) was carefully added. After stirring for 15 min at room temperature, the solvent was evaporated under reduced pressure. More methanol was added and the process was repeated three times. The resulting gray solid was recrystallized from ethanol-ethyl acetate to yield a total of 12 mg (41%) of the hydrobromide salt of compound 4: mp 258° C. (dec); $^1$H NMR (HBr salt, CD$_3$OD) δ3.43 (t, 1H, J=12 Hz, H-1a), 3.48 (dd, 1H, J=3.5, 18 Hz, H-1b), 4.04 (m, 1H, H-11b), 4.38 (dd, 2H, J=5.5, 12 Hz, H-7), 4.44 (s, 2H, H-3), 6.58 (d, 1H, J=8.5 Hz, ArH), 6.71 (d, 1H, J=8.5 Hz, ArH), 7.11 (d, 1H, J=7.5 Hz, ArH), 7.25 (t, 1H, J=7.5 Hz, ArH), 7.32 (d, 1H, J=7.5 Hz, ArH); MS (CI) m/z 254 (100); HRCIMS Calculated for $C_{16}H_{15}NO_2$: 254.1181; Found 254.1192.

Pharmacology of Dinapsoline

Methods

Adult male Sprague Dawley rats (200–250 g) were obtained from Charles River Breeding Laboratories (Raleigh, N.C.) or Harlan Laboratories (Indianapolis, Ind.). Rats were killed by decapitation, and the whole brains removed and chilled briefly in ice-cold saline. Brains were sliced with the aid of a dissecting block, and central striata were then dissected from two coronal sections containing the majority of this region. Tissue was frozen immediately on dry ice and stored at -70° C. until the day of the assay.

Cell Cultures

C-6 glioma cells expressing the rhesus macaque $D_1A$ receptor, (C-6-mD$_{1A}$; Machida et al., 1992) were grown in DMEM-H medium containing 4,500 mg/L glucose, L-glutamine, 5% fetal bovine serum and 600 ng/mL G418 or 2 μg/mL puromycin. Cells were maintained in a humidified incubator at 37° C. with 5% CO$_2$.

Membrane Preparation

Cells were grown in 75 cm$^2$ flasks until confluent. The cells were rinsed and lysed with 10 mL of ice cold hypoosmotic buffer (HOB) (5 mM Hepes, 2.5 mM MgCl$_2$, 1 mM EDTA; pH 7.4) for 10 minutes at 4° C. Cells were then scraped from the flasks using a sterile cell scraper from Baxter (McGaw Park, Ill.). Flasks received a final rinse with 5 mL of HOB. The final volume of the cell suspension recovered from each flask was ca. 14 mL. Scraped membranes from several flasks were then combined. The combined cell suspension was homogenized (10 strokes), 14 mL at a time, using a 15 mL Wheaton Teflon-glass homogenizer. The cell homogenates were combined and spun at 43,000×g (Sorvall RC-5B/SS-34, Du Pont, Wilmington, Del.) at 4° C. for 20 min. The supernatant was removed, and the pellet was resuspended (10 strokes) in 1 mL of ice cold HOB for each original flask of cells homogenized. This homogenate was then spun again at 43,000×g at 4° C. for 20 min. The supernatant was removed and the final pellet was resuspended (10 strokes) in ice cold storage buffer (50 mM Hepes, 6 mM MgCl$_2$, 1 mM EDTA; pH 7.4) to yield a final concentration of ca. 2.0 mg of protein/mL. Aliquots of the final homogenate were stored in microcentrifuge tubes at -80° C. Prior to their use for adenylate cyclase assays, protein levels for each membrane preparation were quantified using the BCA protein assay reagent (Pierce, Rockford, Ill.) adapted for use with a microplate reader (Molecular Devices; Menlo Park, Calif.).

Dopamine Receptor Binding Assays

Frozen rat striata were homogenized by seven manual strokes in a Wheaton Teflon-glass homogenizer in 8 mL ice cold 50 mM HEPES buffer with 4.0 mM MgCl$_2$ (pH 7.4). Tissue was centrifuged at 27,000×g for 10 min, the supernatant was discarded, and the pellet was homogenized (five strokes) and resuspended in ice cold buffer and centrifuged again. The final pellet was suspended at a concentration of 2.0 mg wet weight/mL. The amount of tissue added to each assay tube was 1.0 mg, in a final assay volume of 1.0 mL. D$_1$ receptors were labeled with [$^3$H]SCH23390 (0.30 nM); D$_2$ receptors were labeled with [$^3$H]spiperone (0.07 nM); unlabeled ketanserin (50 nM) was added to mask binding to 5-HT$_2$ sites. Total binding was defined as radioligand bound in the absence of any competing drug. Nonspecific binding was estimated by adding unlabeled SCH23390 (1 μM) or unlabeled chlorpromazine (1 μM) for D$_1$ and D$_2$ receptor binding assays, respectively. As an internal standard, a competition curve with six concentrations of unlabeled SCH23390 ($D_1$ binding) or chlorpromazine ($D_2$ binding) was included in each assay. Triplicate determinations were made for each drug concentration. Assay tubes were incubated at 37° C. for 15 minutes, and binding was terminated by filtering with ice cold buffer on a Skatron 12 well cell harvester (Skatron, Inc., Sterling, Va.) using glass fiber filter mats (Skatron no. 7034). Filters were allowed to dry and 1.0 mL of Optiphase HI-SAF II scintillation fluid were added. Radioactivity was determined on an LKB Wallac 1219 RackBeta liquid scintillation counter (Wallac, Gaithersburg, Md.). Tissue protein levels were estimated using the BCA protein assay reagent (Pierce, Rockford, Ill.).

Data Analysis for Radioreceptor Assays

Binding data from each assay were analyzed separately. Data were normalized by expressing the average dpm at each competitor concentration as a percentage of total binding. These data were then subjected to nonlinear regression analysis using the algorithm for sigmoid curves in the curve-fitting program InPlot (Graphpad Inc.; San Francisco, Calif.) or EBDA and LIGAND software, as adapted for the IBM-PC by McPherson, to generate Ko. values and a Hill coefficient ($n_H$) for each curve. Analysis of the residuals indicated an excellent fit; r values were above 0.99 for all curves in the present experiments.

Adenylate Cyclase Activity in Rat Striatum

The automated HPLC method of Schulz and Mailman was used to measure adenylate cyclase activity by separating cAMP from other labeled nucleotides. Briefly, striatal tissue from rat was homogenized with eight manual strokes in a Wheaton-Teflon glass homogenizer in 5 mM HEPES buffer (pH 7.5) containing 2 mM EGTA (50 mL/g tissue). Following the addition and mixing of 50 mL/g of 50 mM HEPES buffer (pH 7.5) containing 2 mM EGTA, a 20 µL aliquot of this tissue homogenate was added to a prepared reaction mixture (final volume of 100 µL) containing 0.5 mM ATP, 0.5 mM isobutyl methylxanthine, [$^{32}$P]ATP (0.5 µCi), 1 mM cAMP, 2 mM $MgCl_2$, 100 mM HEPES buffer, 2 µM GTP, 0–100 AM dopamine, DHX, or SKF38393, 10 mM phosphocreatine and 5 U creatine phosphokinase. Triplicate determinations were performed for each drug concentration.

The reaction proceeded for 15 min at 30° C. and was terminated by the addition of 100 µL of 3% sodium dodecyl sulfate (SDS). Proteins and much of the non-cyclic nucleotides were precipitated by addition of 300 µL each of 4.5% $ZnSO_4$ and 10% $Ba(OH)_2$. Samples were centrifuged (10,000×g for 8–9 min), and the supernatants injected on an HPLC system (Waters Z-module or RCM 8×10 module equipped with a C18, 10 micron cartridge). The mobile phase was 150 mM sodium acetate (pH 5.0) with 23% methanol. A UV detector (254 nm detection) was used to quantify the unlabeled cAMP added to the samples to serve as internal standard. The radioactivity in each fraction was determined by a flow-through radiation detector (Inus Systems, Tampa, Fla.) using Cerenkov counting. Sample recovery was based on UV measurement of total unlabeled cAMP peak areas quantified using PE Nelson (Cupertino, Calif.) Model 900 data collection modules and TurboChrom software. Tissue protein levels were estimated using the BCA protein assay reagent (Pierce, Rockford, Ill.).

Adenylate Cyclase Assay in C-6m$D_{1A}$ Cells

Frozen membranes were thawed and added to assay tubes (10 µg protein/tube) containing a prepared reaction mixture [100 mM Hepes, (pH 7.4), 100 mM NaCl, 4 mM $MgCl_2$, 2 mM EDTA, 500 µM isobutyl methylxanthine (IBMX), 0.01% ascorbic acid, 10 µM pargyline, 2 mM ATP, 5 µM GTP, 20 mM phosphocreatine, 5 units of creatine phosphokinase (CPK), 1 µM propranolol] and selected drugs. The final reaction volume was 100 µL.

Basal cAMP activity was determined by incubation of tissue in the reaction mixture with no drug added. Tubes were assayed in duplicate and, after a 15 min incubation at 30° C., the reaction was stopped by the addition of 500 µL of 0.1 N HCl. Tubes were vortexed briefly, and then spun in a BHG HermLe Z 230 M microcentrifuge for five min at 15,000×g to precipitate particulates.

Radioimmunoassay (RIA) of cAMP

The concentration of cAMP in each sample was determined with an RIA of acetylated cAMP, modified from that previously described. Iodination of cAMP was performed using a method reported by Patel and Linden. Assay buffer was 50 mM sodium acetate buffer with 0.1% sodium azide (pH 4.75). Standard curves of cAMP were prepared in buffer at concentrations of 2 to 500 fmol/assay tube. To improve assay sensitivity, all samples and standards were acetylated with 10 µl of a 2:1 solution of triethylamine:acetic anhydride. Samples were assayed in duplicate. Each assay tube (total volume 300 µL) contained 25 µL of each sample, 75 µL of buffer, 100 µL of primary antibody (sheep, anti-cAMP, 1:100,000 dilution with 1% BSA in buffer) and 100 µL of [$^{125}$I]-cAMP (50,000 dpm/100 µL of buffer). Tubes were vortexed and stored at 4° C. overnight (approx. 18 h). Antibody-bound radioactivity was separated by the addition of 25 µL of BioMag rabbit, anti-goat IgG (Advanced Magnetics, Cambridge Mass.), followed by vortexing and incubation at 4° C. for 1 h. To these samples 1 mL of 12% polyethylene glycol/50 mM sodium acetate buffer (pH 6.75) was added and tubes were centrifuged at 1700×g for 10 min. Supernatants were aspirated and radioactivity in the pellet was determined using an LKB Wallac gamma counter (Gaithersburg, Md.).

Data Analysis for Adenylate Cyclase Studies

Data for each sample were expressed initially as pmol/mg/min cAMP. Baseline values of cAMP were subtracted from the total amount of cAMP produced in each drug condition. Data for each drug were expressed relative to the stimulation produced by 100 µM DA.

Results

Binding and Functional Effects of Dinapsoline at $D_1$ Receptors in Rat Striatal Homogenates As shown in FIG. 3, dinapsoline competed with high affinity at $D_1$ receptors in rat striatal homogenates, having almost identical affinity as dihydrexidine, a full $D_1$ agonist. Both dinapsoline and dihydrexidine had shallower slopes for their competition curves than did the prototypical $D_1$ antagonist SCH23390 (1).

Table 1. summarizes the affinities of (+)-3 and (±)-4 at dopamine receptors in rat brain. Radioligand binding studies for dopamine receptors were conducted in rat striatal homogenates, using 0.3 nM $^3$H-SCH23390 ($D_1$ sites) and 0.07 nM $^3$H-spiperone in the presence of 50 nM unlabeled ketanserin ($D_2$ sites). Competition curves were analyzed by non linear regression to determine estimates for the $K_{0.5}$ and Hill slope ($n_H$). Data represent the mean and standard error from three independent assays for each test compound.

TABLE 1

Summary of affinities of (+)-3 and (±)-4 at dopamine receptors in rat brain.

| Compound | D1 binding K0.5(nM) | nH | D2 binding K0.5(nM) | nH |
|---|---|---|---|---|
| (±)-4 | 5.93 ± 0.45 | 0.66 ± 0.01 | 31.3 ± 4.4 | 0.71 ± 0.03 |
| (+)-3 | 4.59 ± 0.28 | 0.65 ± 0.01 | 43.2 ± 3.2 | 0.72 ± 0.04 |
| (+)-2 | 17 ± 4 | 0.75 ± 0.08 | Not Tested | — |
| (+)-1 | 0.30 ± 0.01 | 1.05 ± 0.01 | Not Tested | — |
| Chlorpromazine | Not Tested | — | 0.92 ± 0.12 | 0.93 ± 0.01 |

Figure 4:
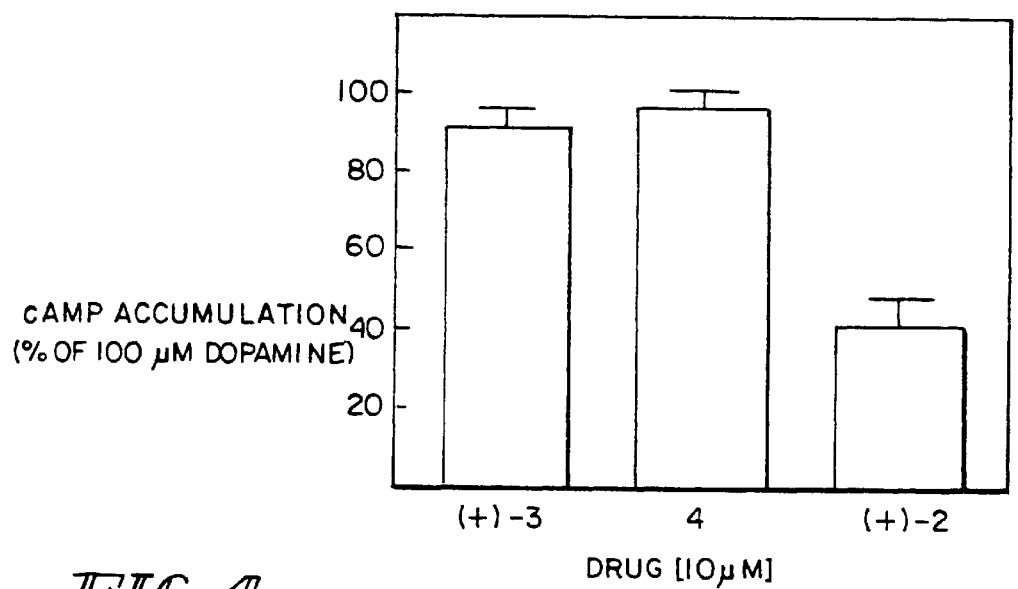
FIG. 4 is a graphic representation of the ability of dinapsoline (4), (+)-dihydrexidine [(+)-3] and (+)-SKF38393 [(+)-2] to stimulate cAMP accumulation in rat striatal homogenates relative to dopamine.

The ability of the test compounds [(+)-SKF38393=(+)-2; (±)-trans-10,11-dihydroxy-5,6,6a,7,8,12b-hexahydrobenzo[a]phenanthridine=(±)-3; and (±)-8,9-dihydroxy-2,3,7,11b-tetrahydro-1H-naphtho[1,2,3-de]isoquinoline=4] to stimulate CAMP accumulation was examined in rat striatal homogenates. The high affinity full agonist (±)-3 and the partial agonist (+)-2 were included for comparison. The data from these experiments is shown in FIG. 4 as the mean ± SEM from at least three experiments. Saturating concentrations (10 $\mu$M) of both dinapsoline and dihydrexidine caused the same degree of increase in cAMP synthesis (95.8%±4.7 for dinapsoline and 91.3%±4.6 for dihydrexidine) as did a maximally effective concentration of dopamine (100 $\mu$M). Conversely, the partial agonist (+)-2 caused less than 50% stimulation (40.7±7.0 for SKF38393). These effects were blocked by the $D_1$ antagonist SCH23390.

Figure 5:
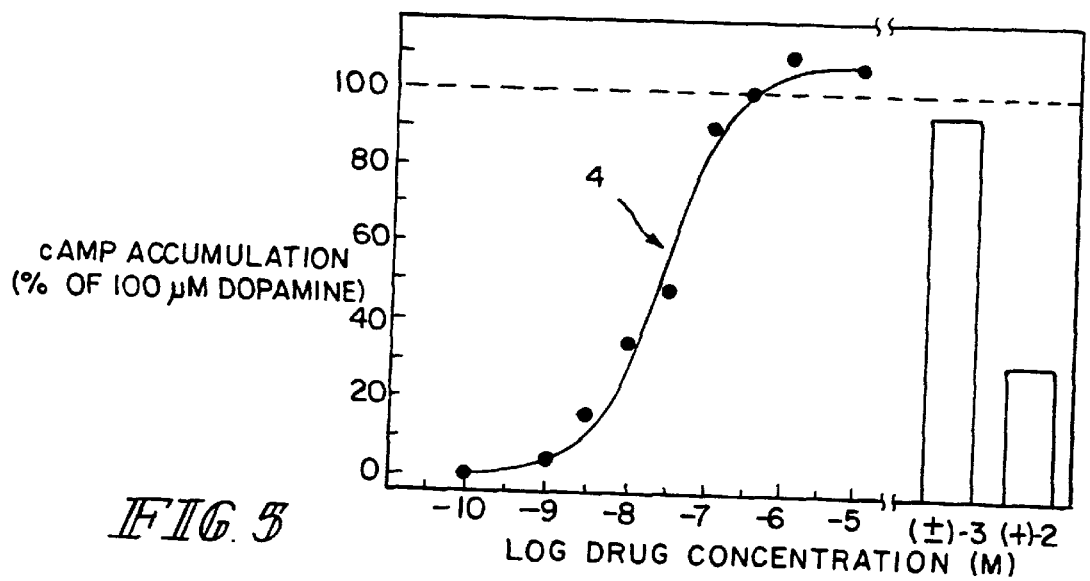
FIG. 5 is a graphic representation of the ability of dinapsoline (4), (+)-dihydrexidine [(+)-3] and (+)-SKF38393 [(+)-2] to stimulate cAMP accumulation in C-6 glioma cells (expressing primate $D_{1A}$ receptors) relative to dopamine.

The functional efficacy of dinapsoline was also tested in cloned primate DIA receptors expressed in C-6 glioma cells (C-6-m$D_1$ cells). As shown in FIG. 5, the compound dinapsoline also exhibited full efficacy in this preparation, with an $EC_{50}$ of ca. 30 nM (data represent the average of two experiments conducted in duplicate). (+)-trans-10,11-dihydroxy-5,6,6a,7,8,12b-hexahydrobenzo[a]phenanthridine (dihydrexidine) also exhibited full efficacy in this preparation, whereas (+)-2 was only of partial efficacy.

Binding at $D_2$ Receptors

Figure 6:
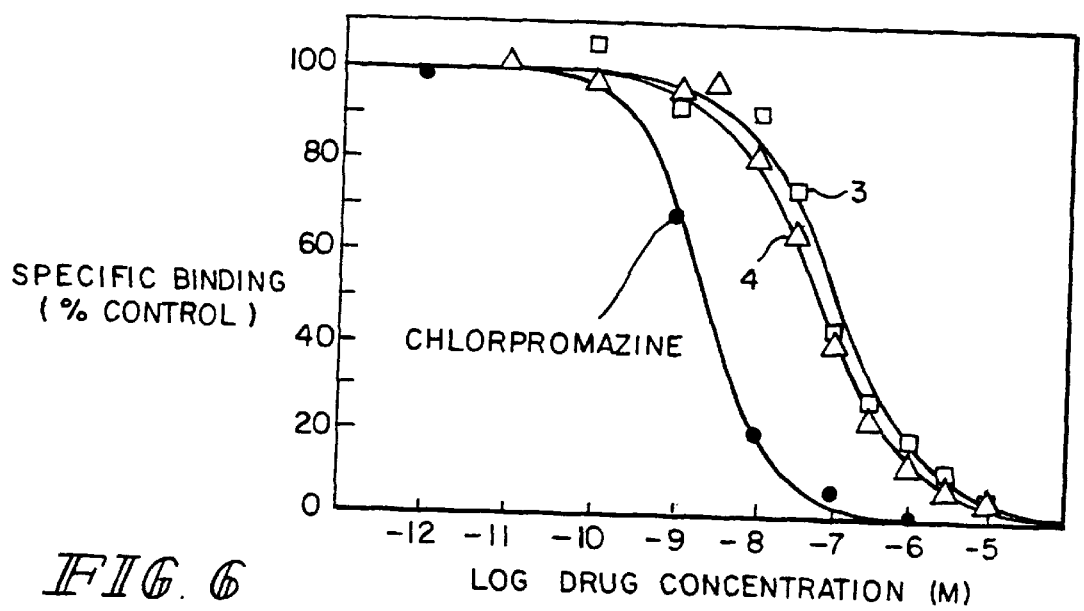
FIG. 6 is a graphic representation of the affinity of dinapsoline (triangles), (+)-dihydrexidine (squares) and (+)-SCH23390 (solid circles) for striatal $D_2$ receptors. Rat striatal $D_2$ receptors were labeled with [$^3$H]SCH23390, and unlabeled dinapsoline, (+)-dihydrexidine or (+)-SCH23390 was added to determine the specific binding of each compound for the $D_2$ receptor.

The ability of dinapsoline to compete for $D_2$ receptors in rat striatal homogenates was investigated. As is shown in FIG. 6 and Table 1, the affinity of dinapsoline for $D_2$-like receptors in rat striatal homogenates ($K_{0.5}$=31 nM) is actually higher than the affinity of dihydrexidine for the $D_2$-like receptors ($K_{0.5}$=50 nM). As can also be seen in FIG. 6, the slope of the competition curves for both dinapsoline and dihydrexidine was shallower than for the prototypical $D_2$ antagonist chlorpromazine.

Using the same general procedures described in Example 1 above, the compounds of Examples 2–48 as set forth in Table II below are synthesized using starting compounds corresponding to those illustrated in Schemes 1 and 2 (FIGS. 1 and 2), but substituted with functional groups appropriate to provide the substitution patterns depicted on the fused naph-isoquinoline product shown for each Example. Thus, for example, 3, 4 and/or 5 substituted analogs of compound 5a (scheme 1) provide the corresponding substituents $R_4$, $R_3$, and $R_2$, respectively, on Formula I. Substitution of N-methyl alanine or N-methyl valine esters for the sarcosine ester in Step b of Scheme I will provide the corresponding compounds of Formula I wherein $R_5$, is methyl and isopropyl, respectively. Use of other 2 and 3 substituted benzamides (analogs of compound 8 in scheme 2) provided corresponding substitution patterns at C8 and C9 in Formula I.

| Example Number | R | $R_1$ | $R_2$ | $R_3$ | $R_4$ | $R_5$ | X |
|---|---|---|---|---|---|---|---|
| 2 | H | H | $CH_3$ | H | H | H | OH |
| 3 | H | H | H | $CH_3$ | H | H | OH |
| 4 | H | H | H | H | $CH_3$ | H | OH |
| 5 | H | H | $C_6H_5$ | H | H | H | OH |
| 6 | $CH_3$ | H | $CH_3$ | H | H | H | OH |
| 7 | $C_3H_7$ | H | H | $CH_3$ | H | H | OH |
| 8 | H | H | $C_2H_5$ | H | H | H | OH |
| 9 | H | H | H | $C_2H_5$ | H | H | OH |
| 10 | H | H | H | $CH_3$ | $CH_3$ | H | Br |
| 11 | $C_3H_7$ | H | $CH_3$ | $CH_3$ | H | H | OH |
| 12 | $C_2H_5$ | H | H | $CH_3$ | $CH_3$ | H | Br |
| 13 | $CH_3$ | H | H | H | $C_2H_5$ | H | OH |
| 14 | $C_4H_9$ | H | H | OH | H | H | OH |
| 15 | H | H | $CH_3$ | OH | H | H | OH |
| 16 | H | H | H | F | H | H | OH |
| 17 | H | H | OH | H | H | H | Br |
| 18 | H | H | Br | H | H | H | OH |
| 19 | H | $CH_3$ | H | Br | H | H | $OCH_3$ |
| 20 | H | $CH_3$ | H | H | Br | H | $OCH_3$ |
| 21 | H | $CH_3$ | $CH_3$ | Br | H | H | $OCH_3$ |
| 22 | $CH_3$ | H | F | H | H | H | OH |
| 23 | $CH_3$ | H | H | F | H | H | OH |
| 24 | $CH_3$ | H | H | H | F | H | OH |
| 25 | $C_2H_5$ | H | H | OH | H | H | F |
| 26 | $C_2H_5$ | H | $CH_3$ | OH | H | H | F |
| 27 | $C_2H_5$ | H | $CH_3O$ | H | $CH_3$ | H | F |
| 28 | $C_3H_7$ | H | H | $CH_3O$ | H | H | Cl |
| 29 | $C_3H_7$ | H | H | $CH_3$ | $CH_3O$ | H | Cl |
| 30 | $C_3H_7$ | H | $C_2H_5O$ | H | H | H | OH |
| 31 | $C_3H_7$ | H | H | H | OH | H | OH |
| 32 | $C_4H_9$ | H | $CH_3$ | H | H | H | OH |
| 33 | $C_4H_9$ | H | H | OH | $CH_3$ | H | OH |
| 34 | $C_4H_9$ | H | OH | Cl | H | H | OH |
| 35 | $C_4H_9$ | H | OH | Cl | H | H | OH |
| 36 | $C_4H_9$ | H | H | $CH_3$ | H | H | I |
| 37 | H | H | H | H | H | H | H |
| 38 | H | H | $CH_3$ | H | H | H | H |
| 39 | H | H | H | $CH_3$ | H | H | H |
| 40 | H | H | H | H | $CH_3$ | H | H |
| 41 | H | H | H | H | H | $CH_3$ | OH |
| 42 | H | H | H | H | H | $CH_2(CH_3)_2$ | OH |
| 43 | H | H | H | H | H | $CH_3$ | H |
| 44 | H | H | H | H | H | $CH_2(CH_3)_2$ | H |
| 45 | H | H | $CH_3$ | H | H | $CH_3$ | OH |
| 46 | H | H | H | $CH_3$ | H | $CH_3$ | OH |
| 47 | H | H | H | H | $CH_3$ | $CH_3$ | OH |
| 48 | H | H | H | H | H | $CH_2CH_3$ | OH |

The foregoing examples are illustrative of the invention and are not intended to limit the invention to the disclosed compounds. Variations and modifications of the exemplified compounds obvious to one skilled in the art are intended to be within the scope and nature of the invention as specified in the following claims.

We claim:

1. A compound of the formula

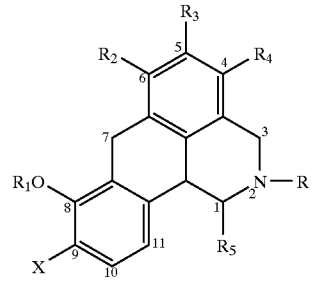

or a pharmaceutically acceptable salt thereof wherein
R, $R_1$ and $R_5$ are independently hydrogen or $C_1$–$C_4$ alkyl;

X is hydrogen, halo or a group of the formula $-OR_6$ wherein $R_6$ is hydrogen or $C_1-C_4$ alkyl, and further when X is a group of the formula $-OR_6$, the groups $R_1$ and $R_6$ can be taken together to form a group of the formula $-CH_2-$; and $R_2$, $R_3$ and $R_4$ are independently selected from the group consisting of hydrogen, $C_1-C_4$ alkyl, phenyl, halo, and $-OR_1$, with the proviso that at least one of $R_2$, $R_3$ and $R_4$ is H and when R is methyl and $R_1$, $R_2$, $R_3$, $R_4$ and $R_5$ are hydrogen, X is not halo.

2. The compound of claim 1, wherein X is hydroxy and $R_1$ is hydrogen.

3. The compound of claim 1, wherein R and $R_5$ are hydrogen.

4. The compound of claim 2, wherein R and $R_5$ are hydrogen.

5. The compound of claim 1 wherein $R_2$, $R_3$, $R_4$ and $R_5$ are each hydrogen.

6. The compound of claim 1 wherein X and $R_1$ are hydrogen.

7. The compound of claim 1 wherein $R_5$ is hydrogen.

8. The compound of claim 1 wherein $R_5$ is $C_1-C_4$ alkyl.

9. The compound of claim 1, wherein R and $R_5$ are hydrogen.

10. The compound of claim 9, wherein $R_2$, $R_3$ and $R_4$ are each hydrogen.

* * * * *

UNITED STATES PATENT AND TRADEMARK OFFICE
CERTIFICATE OF CORRECTION

PATENT NO. : 5,959,110
DATED : September 28, 1999
INVENTOR(S) : David E. Nichols et al.

It is certified that error appears in the above-identified patent and that said Letters Patent is hereby corrected as shown below:

Column 1,
Line 11, please delete the paragraph and replace with the following: -- This invention was made with Government support under Grant Nos. MH-42705 and MH-40537 awarded by the National Institutes of Health. The Government has certain rights in the invention. --

Signed and Sealed this

Thirtieth Day of November, 2004

JON W. DUDAS
*Director of the United States Patent and Trademark Office*